(12) United States Patent
Davis et al.

(10) Patent No.: US 12,721,982 B2
(45) Date of Patent: Sep. 1, 2026

(54) DEVICE AND METHOD FOR ADMINISTERING LIQUID TO THE EAR CANAL

(71) Applicant: The Regents of the University of California, Oakland, CA (US)

(72) Inventors: Jill Friend Davis, Novato, CA (US); Andrew N. Goldberg, San Francisco, CA (US); Don Hannula, San Luis Obispo, CA (US)

(73) Assignee: The Regents of the University of California, Oakland, CA (US)

( * ) Notice: Subject to any disclaimer, the term of this patent is extended or adjusted under 35 U.S.C. 154(b) by 618 days.

(21) Appl. No.: 18/023,968

(22) PCT Filed: Aug. 27, 2021

(86) PCT No.: PCT/US2021/071298
§ 371 (c)(1),
(2) Date: Feb. 28, 2023

(87) PCT Pub. No.: WO2022/047488
PCT Pub. Date: Mar. 3, 2022

(65) Prior Publication Data

US 2023/0310818 A1 Oct. 5, 2023

Related U.S. Application Data

(60) Provisional application No. 63/071,865, filed on Aug. 28, 2020.

(51) Int. Cl.
*A61M 31/00* (2006.01)
*A61F 11/00* (2022.01)
(Continued)

(52) U.S. Cl.
CPC ............ *A61M 31/00* (2013.01); *A61F 11/00* (2013.01); *A61M 3/0262* (2013.01);
(Continued)

(58) Field of Classification Search
CPC .......... A61M 31/00; A61M 2210/0662; A61M 11/00; A61M 2202/04; A61M 3/022;
(Continued)

(56) References Cited

U.S. PATENT DOCUMENTS 1,975,545 A * 10/1934 Homewood .......... B65D 35/40 222/424.5
2,197,689 A * 4/1940 Fromm ................ A61M 31/00 604/213
(Continued)

FOREIGN PATENT DOCUMENTS

DE 3636535 A1 * 4/1988 .............. A61F 11/00
WO WO-8504108 A1 * 9/1985 .......... A61M 3/0005

OTHER PUBLICATIONS

International Search Report mailed Dec. 22, 2021, from co-pending PCT Application No. PCT/US21/71298 filed on Aug. 27, 2021.

*Primary Examiner* — Scott J Medway
(74) *Attorney, Agent, or Firm* — Risley IP; David Risley

(57) ABSTRACT

In one embodiment, a delivery device for administering liquid includes a bottle body having a bottle neck, a bottle cap configured to attach to the bottle neck, a nozzle associated with the bottle cap, and a valve assembly associated within the nozzle, the valve assembly comprising a liquid metering valve configured to ensure a precise, predetermined volume of liquid exits the nozzle each time a user actuates the delivery device.

17 Claims, 5 Drawing Sheets

(51) Int. Cl.
*A61M 3/02* (2006.01)
*A61M 39/26* (2006.01)
*G01F 11/26* (2006.01)

(52) U.S. Cl.
CPC ........... *A61M 39/26* (2013.01); *G01F 11/265* (2013.01); *A61M 2210/0662* (2013.01)

(58) Field of Classification Search
CPC .. A61M 3/0233; A61M 3/0262; A61M 39/22; A61M 11/008; A61F 11/00; A61F 11/006; A61H 2205/027
See application file for complete search history.

(56) References Cited

U.S. PATENT DOCUMENTS 2,730,270 A * 1/1956 Heinemann ........... G01F 11/286 222/207
2,942,762 A * 6/1960 Fahr ...................... B05B 11/007 222/207
2,979,236 A * 4/1961 Fahr ........................ G01F 11/08 222/207
3,705,668 A * 12/1972 Schwartzman .... B65D 47/2075 222/207
3,878,972 A * 4/1975 Por ....................... G01F 11/288 222/207
4,625,897 A * 12/1986 Wortley ................ G01F 11/286 222/207
4,875,603 A 10/1989 Weinstein
5,125,543 A * 6/1992 Rohrabacher ......... B05B 11/047 222/211
5,127,553 A 7/1992 Weinstein
5,505,193 A * 4/1996 Ballini ................... A61H 35/04 128/200.14
6,135,358 A * 10/2000 Ballini ................ A61M 3/0233 239/348
6,186,367 B1 2/2001 Harrold
6,675,845 B2 * 1/2004 Volpenheim ............ G01F 19/00 141/381
7,699,820 B1 * 4/2010 French ................ A61M 3/0216 604/35
8,708,203 B2 * 4/2014 Laible .................. B65D 47/122 222/481.5
8,991,660 B2 * 3/2015 Hair ......................... B65D 1/32 222/211
12,358,698 B2 * 7/2025 Prodromou .......... B65D 50/048
2003/0229322 A1 12/2003 Macrae
2008/0195038 A1 8/2008 Hill et al.
2010/0312199 A1 * 12/2010 Lu ............................ A47K 7/08 604/279
2013/0310805 A1 * 11/2013 Yadidi .................. A61M 11/005 604/514
2015/0119856 A1 4/2015 Vlodaver et al.

* cited by examiner

DEVICE AND METHOD FOR ADMINISTERING LIQUID TO THE EAR CANAL

CROSS REFERENCE TO RELATED APPLICATIONS

This application is a 35 U.S.C. § 371 national stage application of PCT Application No. PCT/US2021/071298, filed Aug. 27, 2021, which claims priority to U.S. Provisional Application Ser. No. 63/071,865, filed Aug. 28, 2020, both of which are hereby incorporated by reference herein in their entireties.

BACKGROUND

In certain circumstances, it is necessary or desirable to deliver liquid to the ear canal. For example, such liquids may contain medication and/or a desiccant to treat an infection in the ear, such as one caused by swimmer's ear. Liquids, typically in drop form, are normally administered using a simple squeeze bottle having a flexible body and a nozzle. In such a case, a user can self-administer the drop(s) by tilting one's head to the side, inverting the bottle, placing the nozzle at or within the ear canal, and squeezing the flexible body to cause one or more drops to exit the nozzle and drop down into the ear canal.

While such squeeze bottles have been used for decades, they have some significant drawbacks. First, it can be difficult for the user to locate the ear canal when self-administering the drops. This can lead to misplacement of the drops as well as wasting of the liquid within the bottle. Second, it can be difficult for the user to administer the correct amount of liquid to the ear canal, whether self-administering or administering the liquid to another person. This can occur due to various factors, such as the design of the squeeze bottle, the angle at which the user is tilting the bottle, as well as difficulty in determining how hard and/or how long to squeeze the bottle to deliver the correct volume of liquid.

In view of the above drawbacks, it can be appreciated that it would be desirable to have a delivery device for administering liquid into the ear canal that both assists the user in locating the ear canal and that is capable of delivering precise volumes of liquid each time the device is used.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a delivery device for administering liquid to the ear canal that both assists the user in locating the ear canal and is capable of delivering precise volumes of liquid each time the device is used. Disclosed herein is an example of such a device and a method with which the device can be used. In some embodiments, the device comprises a flexible bottle body, a bottle cap configured to attach to a neck of the bottle, an ear canal locating element associated with a nozzle of the cap, and a liquid metering valve configured to deliver a precise, predetermined volume of liquid each time the user actuates the bottle.

In the following disclosure, various specific embodiments are described. It is to be understood that those embodiments are example implementations of the disclosed inventions and that alternative embodiments are possible. Such alternative embodiments include hybrid embodiments that include features from different disclosed embodiments. All such embodiments are intended to fall within the scope of this disclosure.

Figure 1:
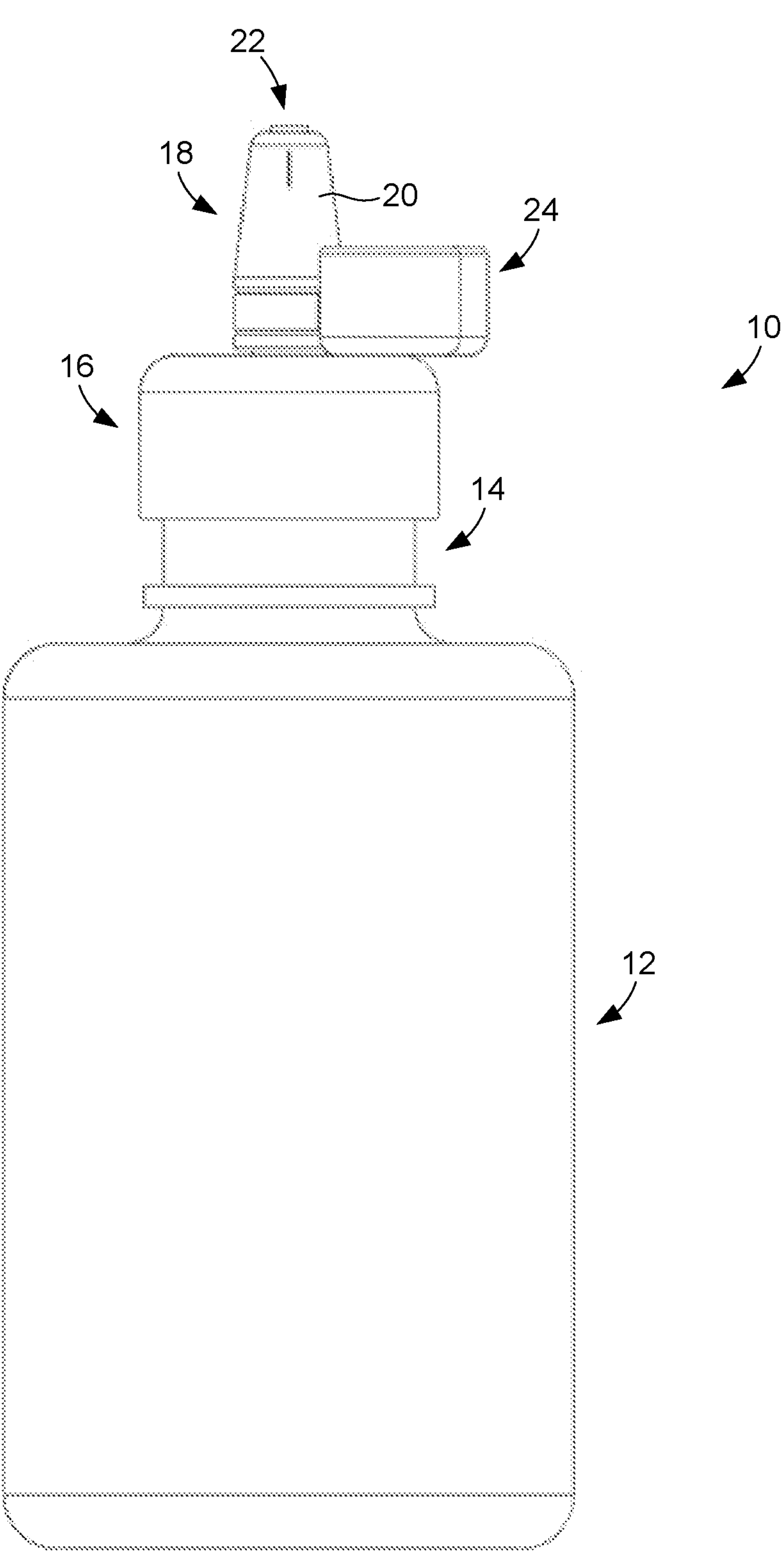
FIG. 1 is a side view of an embodiment of a device for administering liquid to the inner ear canal.

FIG. 1 illustrates an embodiment of a delivery device 10 for administering liquid to the ear canal. As shown in this figure, the device 10 generally comprises a bottle body 12 having a threaded bottle neck 14, a bottle cap 16 that is configured to thread onto the neck, a valve assembly 18 of which a nozzle 20 and a vent tube 22 are visible in FIG. 1, and an ear canal locating element 24 that, as shown in the figure, can be attached to the nozzle. In some embodiments, each of these components is made of a suitable polymeric material. Regardless, the bottle body 12 is made of a flexible material that enables a user to squeeze the body to administer a precise volume (e.g., drop) of liquid into the user's ear canal and that returns to its original shape when released.

Figure 2:
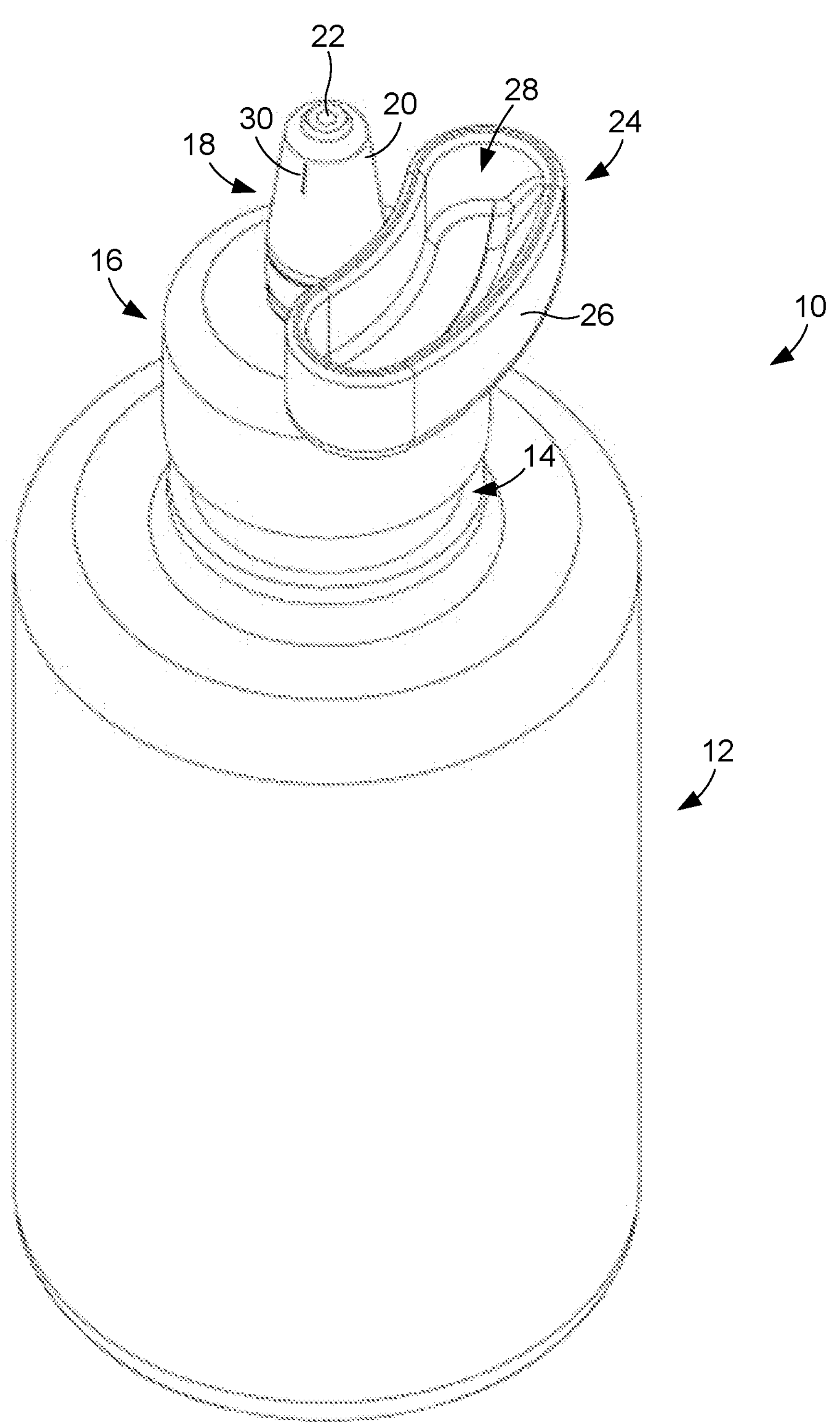
FIG. 2 is a perspective view of the device of FIG. 1.

FIG. 2 is a perspective view of the delivery device 10 that more clearly illustrates the ear canal locating element 24. As is apparent from this figure, the locating element 24 is includes a cup 26 that is configured to receive the tragus of the outer ear. In view of this functionality, the locating element 24 can also be referred to as a "tragus cup." The cup 26 faces upward (when the device 10 is in the upright configuration shown in FIG. 1) and includes a cavity 28 in which the tragus can be received. As shown in FIG. 2, the cup 26 as well as its cavity 28 can have a kidney or bean shape when viewed from above or below. This shape is useful as the tragus typically has a curvature that is accommodated by the shape.

Irrespective of its particular configuration, the ear canal locating element 24 assists the user in positioning the nozzle 20 at or within the ear canal before liquid is administered. Specifically, the cavity 28 of the element 24 is laterally spaced from the nozzle 20 a pre-determined distance (e.g., 1-2 cm) such that, when cup 26 is placed over the tragus of the ear, the nozzle will be aligned with the entrance to the ear canal. As it is much easier for users to locate their tragus, as opposed to the ear canal, the element 24 assists the user in correctly positioning the nozzle 20 and administering liquid within the ear canal.

Also visible in FIG. 2 is one of multiple lateral slits 30 that are formed in the nozzle 20. As described in greater detail below, the liquid that is administered to the ear canal does not flow out from the distal tip of the nozzle 20 in the direction of a central vertical axis of the nozzle, as is typically the case. Instead, the liquid laterally exits the nozzle 20 (generally perpendicular to the nozzle's vertical longitudinal axis) through the slits 30 to avoid discomfort to the user.

Figure 3:
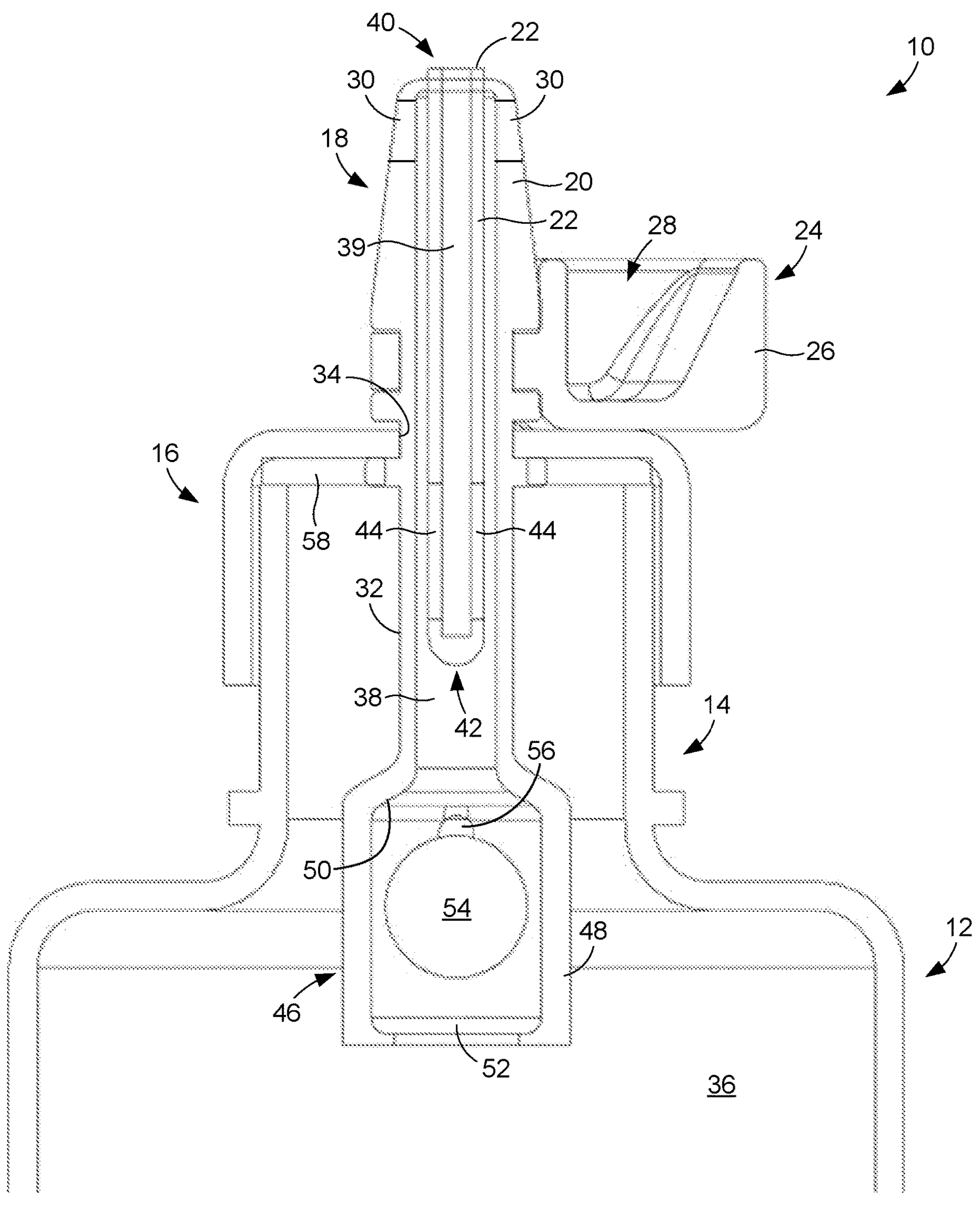
FIG. 3 is partial cross-sectional view of the device of FIG. 1, illustrating an internal liquid metering mechanism.

FIG. 3 is a partial cross-sectional view of the delivery device 10 that illustrates internal components of the valve assembly 18. In the illustrated embodiment, the valve assembly 18 includes the nozzle 20 and vent tube 22 identified above, as well as an elongated cylindrical delivery tube 32 that passes through an opening 34 formed in the bottle cap 16. The delivery tube 32 extends from the nozzle 20, through the neck 14 of the bottle body 12, and into an interior space 36 defined by the body, which is configured to contain liquid that is to be administered to the ear canal. In some embodiments, the nozzle 20 and the delivery tube 32 are unitarily formed from a single piece of a flexible polymeric material, such as silicone, which aids in sealing of a metering valve described below. The delivery tube 32 includes an inner lumen 38 through which the liquid contained in the body 12 can be delivered to the nozzle 20 and, ultimately, the ear canal.

With further reference to FIG. 3, the vent tube 22 can also be configured as an elongated cylindrical tube that includes its own inner lumen 39 through which air can flow into the bottle body 12 to equalize the pressure within the body with the ambient pressure after delivery of liquid. As is apparent from FIG. 3, a top end 40 of the tube 22 can extend beyond the tip of the nozzle 20 and a bottom end 42 of the tube can be located within the lumen 38 of the delivery tube 32. Lateral slits 44 are provided near the bottom end 42 of the vent tube 22 that enable air to flow through the tube and into the interior space 36.

As is further shown in FIG. 3, a bottom portion of the delivery tube 32 defines a liquid metering valve 46 that is configured to precisely control the volume of liquid that can be administered each time the device 10 is actuated by the user. The valve 46 includes a cylindrical valve body 48 that defines an upper valve seat 50 that is open to the remainder of the tube 36 and a lower valve seat 52 that is open to the interior space 34 of the bottle body 12. Both seats 50, 52 are configured to receive a float element 54 that is contained within the valve 46. When the float element 54 is received in either seat 50, 52, a seal can be formed between the element and the valve body 48 such that liquid cannot flow past the element and out through the valve 46 when the element is seated. In the illustrated embodiment, the valve seats 50, 52 are circular and the float element 54 is spherical. Irrespective of its specific configuration, the float element 54 is buoyant such that it floats in liquid. In some embodiments, the float element 54 can be a hollow aluminum sphere.

In addition to the valve seats 50, 52, the valve body 48 also includes one or more lateral vent holes 56 positioned near the upper seat 50 through which air that flows down the vent tube 22 can pass through the metering valve 46 and enter the interior space 36.

Lastly illustrated in FIG. 3 is a sealing gasket 58 that is positioned between the bottle neck 14 and the bottle cap 16. The gasket 58 can be made of an elastic material, such as rubber or silicone, and forms an air- and liquid-tight seal between the neck 14 and cap 16 so that no air or liquid can leak into or out from or into the device 10 during use.

Figure 4A:
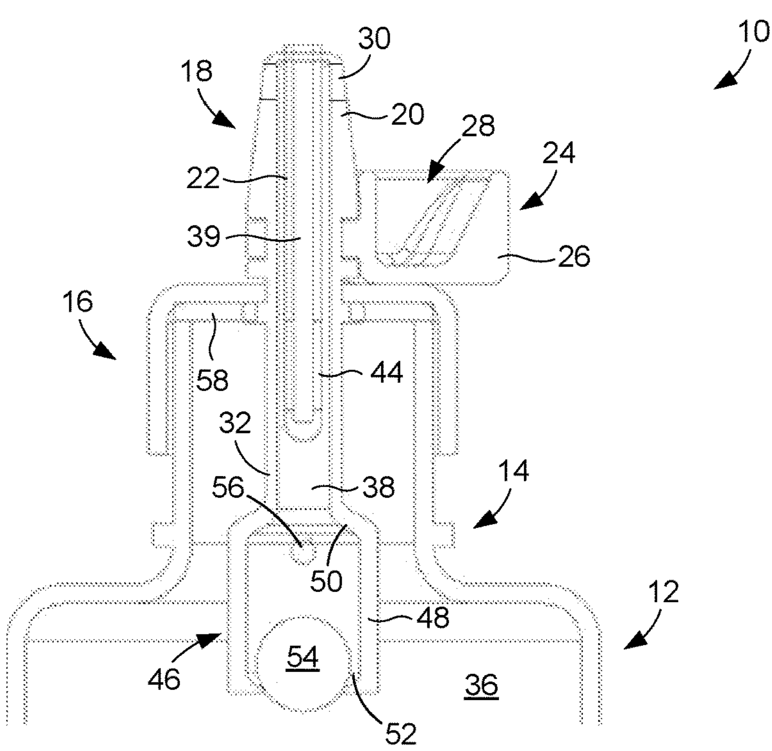
FIG. 4A-4C are partial cross-sectional views of the device of FIG. 1, illustrating use and operation of the device of FIG. 1.
Figure 4B:
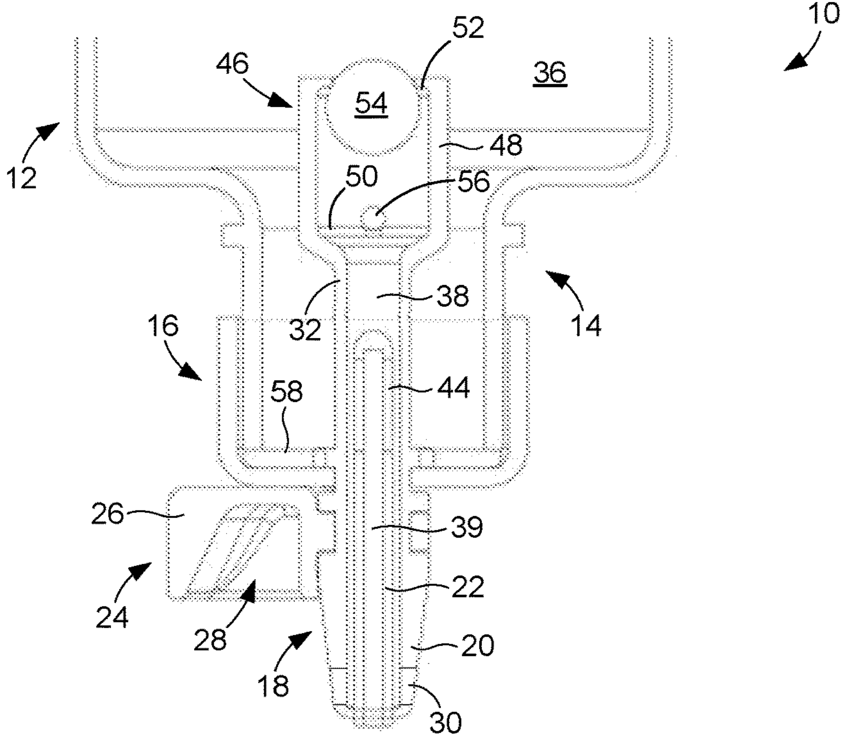
Figure 4C:
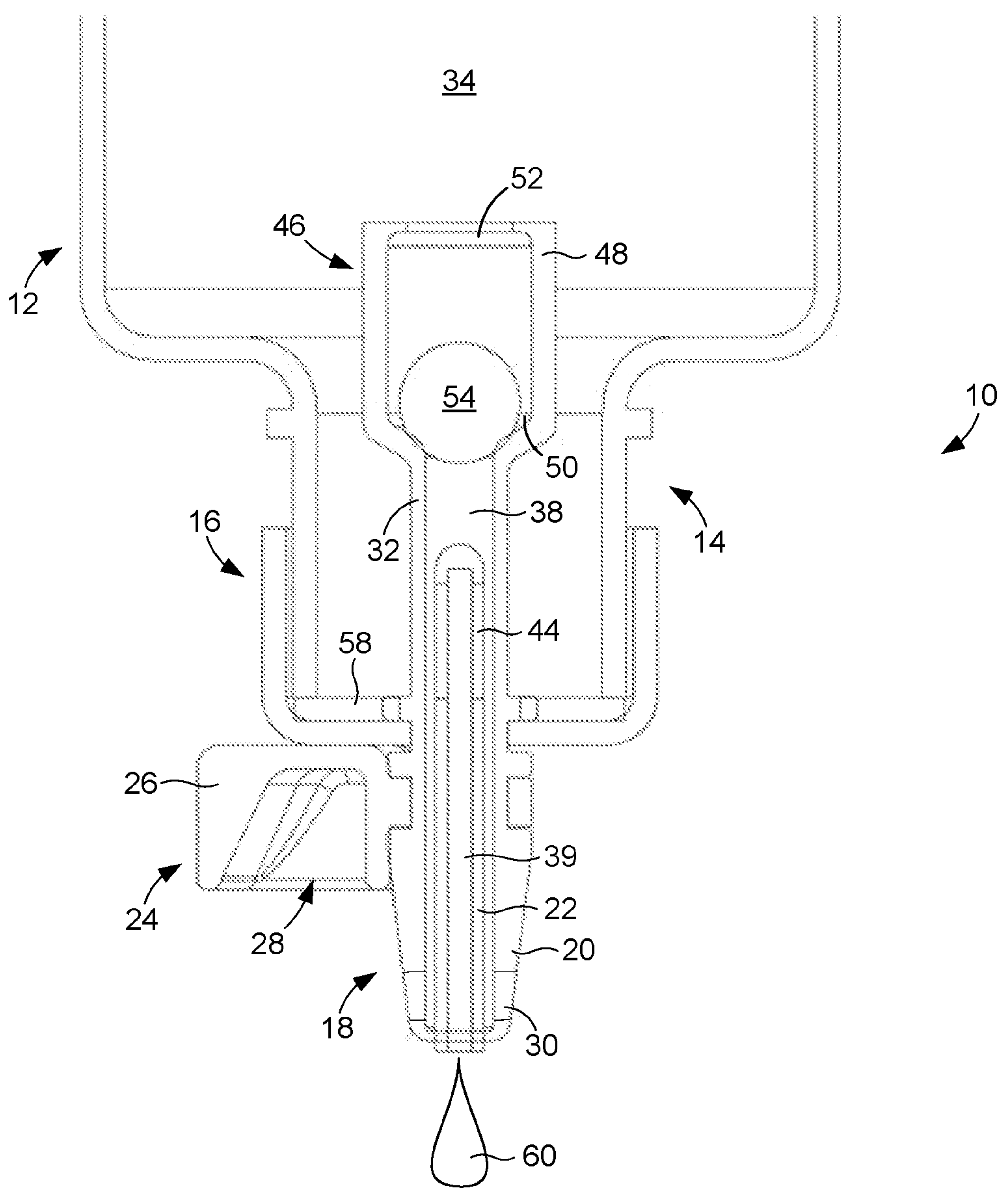

FIGS. 4A-4C illustrate use and operation of the delivery device 10. More particularly, FIG. 4A shows the device 10 in an upright orientation prior to use, FIG. 4B shows the device after being inverted prior to administration of liquid to the ear canal, and FIG. 4C shows the device immediately after liquid has been dispensed from the nozzle, thereby forming a drop 60 of liquid prior to it falling into the ear canal. Beginning with 4A, it is assumed that the level of fluid within the bottle body 12 is below the metering valve 46. In such a case, the float element 54 rests on the lower valve seat 52 under the force of gravity (and in the absence of liquid that would cause it to float).

When liquid is to be administered to the ear canal, the user tilts his or her head to the side to position the ear into which liquid is to be administered generally pointing upward so that liquid drops can drop down into the ear canal. Referring to FIG. 4B, the user inverts the device 10 from the upright orientation of FIG. 4A to prepare the device for administration of liquid. When the device 10 is inverted, liquid within the interior space 36 of the bottle body 12 flows downward under the force of gravity toward the top of the device and fills the delivery tube 32, including the metering valve body 48. When the valve body 48 is filled, the float element 54 floats up to the lower valve seat 52, which, in the inverted orientation, is positioned above the upper valve seat 50, as shown in FIG. 4B.

Next, the user can position the distal tip of the nozzle 20 of the device 10 immediately above or partially within the ear canal. As described above, this positioning can be facilitated through use of the ear canal locating element 24. Specifically, the user can place the cup 26 of the element 24 over the tragus of the ear. When the user does this, the nozzle 20 will be aligned with the ear canal.

With reference next to FIG. 4C, once the nozzle 20 is positioned above/within the ear canal, the user can then actuate the device 10 by gently squeezing the bottle body 12. Doing this increases the pressure within the body 12 and drives the liquid it contains through the lower valve seat 52 and past the float element 54, through the upper portion of the delivery tube 32, and out through the lateral slits 30 of the nozzle 20 so that a drop 60 of liquid collects at the nozzle tip and drops down under the force of gravity into the ear canal. Due to the presence of the metering valve 46, a precise, predetermined volume of liquid is delivered to the ear canal. This volume is substantially equal to the volume of the interior space defined by the delivery tube 32, including the valve body 48. No further liquid is delivered because the increased pressure within the bottle body 12 that results from squeezing forces the float element 54 downward and into firm contact with the upper valve seat 50, thereby closing the valve and preventing further liquid from flowing into the upper portion of the delivery tube 32 and out through the nozzle 20.

Once the liquid drop has been administered and the bottle body 12 is permitted to return to its original shape (e.g., while still in the inverted orientation), the pressure within the bottle body 12 drops below the ambient pressure. This reduced pressure within the body 12 maintains the float element 54 in place against the upper valve seat 50. At the same time, however, air is drawn in through the vent tube 22 and into the bottle body 12 to equalize the pressure within the body with the ambient pressure. The float element 54 is then released from the upper valve seat 50 and the delivery tube 32 again fills with liquid. The float element 54 again floats up through the valve body 48 to seat in the lower valve seat 52, thereby returning to the device 10 the configuration shown in FIG. 4B. If further liquid is to be delivered, the user can simply squeeze the bottle body 12 again and a further drop of substantially the same volume will drop into the ear canal.

In some embodiments, the delivery tube 32 is sized and configured to deliver a pre-determined volume of liquid that is either generally equivalent to the volume of liquid that is to be administered or a fraction thereof. For example, if the volume of the delivery tube 32 is substantially equal to the volume of liquid that is to be administered, the user can deliver a single drop into the ear canal. If, however, a liquid volume equal to two drops is to be administered, the delivery tube 32 can have an interior space that is approximately half of the volume of the liquid to be administered, in which case the user would administer two drops of liquid. This enables the device 10 to be used to deliver different volumes of liquid. For instance, a child may only require a single drop of liquid, whereas an adult may require two or more drops of liquid.

Once the correct dose of liquid has been administered, the user can return the device 10 to its original upright position shown in FIG. 4A. The above process can then be repeated each time the user is to receive another dose of liquid.

Although the above disclosure is focused on delivering liquid to the ear canal, it is noted that the device or portions thereof could be used to administer liquids in other contexts. For example, a device including the valve assembly of the disclosed delivery device could be used to administer precise volumes of liquid to the eye or other body part. In such a case, the ear canal locating element would not be necessary and could be omitted.

The invention claimed is:

1. A delivery device for administering liquid to a patient, the device comprising:

a bottle including a bottle body and a bottle neck;

a bottle cap attached to the bottle neck; and a valve assembly connected to the bottle cap, the valve assembly including a liquid nozzle that extends out from the bottle cap, a liquid metering valve positioned within the bottle body, and a liquid delivery tube that extends from the liquid nozzle, through the bottle cap and the bottle neck, and to the liquid metering valve, wherein liquid contained in the bottle body can travel through the liquid metering valve, the liquid delivery tube, and the liquid nozzle for delivery to the patient, the valve assembly further including an air vent tube that extends through the liquid nozzle and into the liquid delivery tube, wherein air from outside of the bottle can travel through the air vent tube, the liquid delivery tube, and the liquid metering valve, and into the bottle body to equalize pressure within the bottle, wherein the liquid metering valve is configured to enable a predetermined volume of liquid from the bottle body to collect within the valve assembly in preparation for delivery to the patient.

2. The delivery device of claim 1, wherein the bottle body is flexible.

3. The delivery device of claim 1, wherein the bottle neck and the bottle cap are threaded to enable the bottle cap to be screwed onto the bottle neck.

4. The delivery device of claim 1, wherein the liquid nozzle includes lateral slits through which the liquid can exit the device.

5. The delivery device of claim 1, wherein the metering valve comprises a valve body that defines an upper valve seat and a lower valve seat, and a buoyant float element that is contained within the valve body between the valve seats, wherein the valve body and liquid delivery tube fills with the predetermined volume of liquid when the delivery device is inverted, and wherein the predetermined volume of liquid is ejected from the liquid nozzle when the bottle body is squeezed.

6. The delivery device of claim 5, wherein the valve body includes a lateral vent hole through which fluid can pass into and out from the bottle body.

7. The delivery device of claim 1, further comprising an ear canal locating element configured to receive a tragus of the patient's ear in a manner in which, when the tragus is so received, the liquid nozzle is aligned with the patient's ear canal.

8. The delivery device of claim 7, wherein the ear canal locating element comprises a tragus cup having a cavity sized and configured to receive the patient's tragus.

9. The delivery device of claim 1, wherein the bottle cap has an opening through which the liquid delivery tube of the valve assembly passes.

10. The delivery device of claim 1, wherein the liquid nozzle of the valve assembly includes an opening at its tip in which a top end of the air vent tube is positioned.

11. The delivery device of claim 1, wherein the lower valve seat of the liquid metering valve forms an opening through which liquid contained within the bottle body can enter the valve assembly.

12. The delivery device of claim 1, wherein the liquid metering valve and the liquid delivery tube together define an interior space having a volume that is substantially equal to the predetermined volume of liquid to be delivered to the patient.

13. The delivery device of claim 1, wherein the liquid nozzle, liquid delivery tube, and the liquid metering valve of the valve assembly are all unitarily formed from a single piece of material.

14. The delivery device of claim 1, wherein the liquid delivery tube and the air vent tube are cylindrical and wherein the air vent tube is coaxial with the liquid delivery tube.

15. The delivery device of claim 7, wherein the ear canal locating element is mounted to the liquid nozzle of the valve assembly.

16. The delivery device of claim 8, wherein the tragus cup has a kidney or bean shape.

17. A delivery device for administering liquid to a patient, the device comprising:

a bottle including a flexible bottle body and a threaded bottle neck;

a threaded bottle cap screwed onto the bottle neck, the bottle cap including a central opening;

a valve assembly connected to the bottle cap, the valve assembly including a liquid nozzle that extends out from the bottle cap, a liquid metering valve positioned within the bottle body, and a liquid delivery tube that extends from the liquid nozzle, through the central opening of the bottle cap, through the bottle neck, and to the liquid metering valve, wherein the liquid nozzle includes a central opening that extends through its tip and lateral slits that extend through sides of the liquid nozzle, wherein the liquid metering valve includes a valve body that defines an interior space having a lower valve seat at one end, an upper valve seat at another end, and a buoyant float element being contained within the interior space between the valve seats, the valve body further including a vent hole through which fluid can pass into and out from the bottle body, the valve assembly further including an air vent tube that extends through the central opening of the liquid nozzle and into the liquid delivery tube; and an ear canal locating element mounted to the liquid nozzle of the valve assembly, the ear canal locating element being configured to receive a tragus of the patient's ear in a manner in which, when the tragus is so received, the liquid nozzle is aligned with the patient's ear canal, wherein liquid contained in the bottle body fills the liquid metering valve and the liquid delivery tube when the bottle is inverted to collect a predetermined volume of liquid and wherein the predetermined volume of liquid is ejected from the lateral slits of the liquid nozzle when the bottle body is squeezed to deliver the predetermined volume of liquid to the patient, and wherein air from outside of the device can travel through the air vent tube, through the liquid delivery tube, through the liquid metering valve, and into the bottle body after the predetermined volume of liquid has been ejected to equalize pressure within the bottle.

* * * * *